United States Patent [19]

Chan

[11] Patent Number: 4,753,957
[45] Date of Patent: Jun. 28, 1988

[54] SUBSTITUTED 2,4-IMIDAZOLIDINEDIONES AND FUNGICIDAL COMPOSITIONS

[75] Inventor: Hak-Foon Chan, Walnut Creek, Calif.

[73] Assignee: Rohm and Haas Company, Philadelphia, Pa.

[21] Appl. No.: 306,015

[22] Filed: Sep. 28, 1981

[51] Int. Cl.$^4$ ............... A01N 43/50; C07D 233/32
[52] U.S. Cl. .......................... 514/391; 424/45; 424/46; 514/256; 514/307; 514/314; 514/361; 514/372; 514/374; 514/378; 514/383; 514/392; 544/230; 544/335; 546/15; 546/146; 546/176; 546/278; 548/147; 548/214; 548/216; 548/235; 548/247; 548/249; 548/253; 548/269; 548/302; 548/311; 548/312; 548/314; 548/318
[58] Field of Search ............... 548/314, 311, 312, 253, 548/269, 235, 247, 249, 214, 147, 216, 318, 302; 424/273 R, 45, 46; 544/335, 230; 546/176, 146, 278, 15; 514/256, 307, 314, 361, 372, 374, 378, 383, 391, 392

[56] References Cited

U.S. PATENT DOCUMENTS 2,551,134  5/1951  Jennings .................... 548/314
3,846,441  11/1974  Mine et al. ................ 548/314
4,427,438  1/1984  Nagano et al. ............. 548/314

FOREIGN PATENT DOCUMENTS 473113  1/1972  Japan .

OTHER PUBLICATIONS

Shirai, *Chemical Abstracts*, vol. 76 (1972) No. 140,807n.
Satomi et al. *Chemical Abstracts*, vol. 82 (1975) No. 81697a.

*Primary Examiner*—Robert W. Ramsuer
*Attorney, Agent, or Firm*—Barbara V. Maurer; Polly E. Ramstad

[57] ABSTRACT

This invention relates to substituted 2,4-imidazolidinediones, their method of preparation and use as broad spectrum systemic fungicides effective in controlling phytopathogenic fungi such as barley net blotch (*Helminthosporium teres*), bean powdery mildew (*Erysiphi polygoni*), grape downy mildew (*Plasmorpora viticola*), tomato late blight (*Phytophthora infestans*), and wheat stem rust (*Puccinia graminis f. sp. tritici* race 15 B-2.

13 Claims, No Drawings

SUBSTITUTED 2,4-IMIDAZOLIDINEDIONES AND FUNGICIDAL COMPOSITIONS

SUMMARY OF THE INVENTION

This invention relates to substituted 2,4-imidazolidinediones of the formula

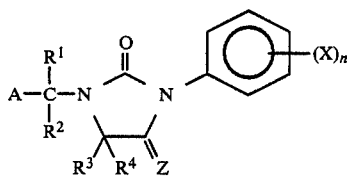

wherein

X represents common phenyl substitutents such as halogen, nitro, cyano, alkyl, alkoxy, trihalomethyl, phenoxy, substituted phenoxy, phenylthio, substituted phenylthio, aralkyl, substituted aralkyl, phenylalkyl, and substituted phenylalkyl;

$R^1$ and $R^2$ are independently hydrogen, alkyl, alkenyl, alkynyl, cyano, halogen, phenyl, phenylalkyl, cycloalkyl, and cycloalkenyl;

$R^3$ and $R^4$ are independently hydrogen, alkyl, alkenyl, alkynyl, cyano, halogen, phenyl, phenylalkyl, cycloalkyl, and cycloalkenyl; or $R^3$ and $R^4$ joined together for a $(C_3-C_8)$cycloalkyl ring or a $(C_3-C_8)$cycloalkenyl ring;

A is phenyl or pseudoaryl, or phenyl or pseudoaryl substituted with up to three substituents selected from the group consisting of halogen, nitro, cyano, $(C_1-C_6)$alkyl, $(C_2-C_6)$alkenyl, $(C_2-C_6)$alkynyl, $(C_1-C_6)$alkoxy, and trihalomethyl, or

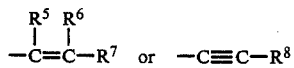

wherein $R^5$, $R^6$, $R^7$, $R^8$ are independently hydrogen, alkyl, alkenyl, alkynyl, phenyl, or halogen, or a phenyl ring, a substituted phenyl ring, or a pseudoaryl ring such as furan or thiophene or a substituted pseudoaryl ring;

n is an integer from 0 to 3;

Z is O, S, NH, or $CH_2$.

These compounds are fungicidal agents active against the spectrum of phytopathogenic fungi.

The term "alkyl", as used in defining substituents in the present specification and claims, include both branched and straight-chain alkyl groups from 1 to 12 carbon atoms. Typical alkyl groups which are encompassed by this term are methyl, ethyl, propyl, isopropyl, n-butyl, sec-butyl, iso-butyl, tert-butyl, pentyl, neopentyl, isopentyl, hexyl, heptyl, isoctyl, nonyl, decyl, isodecyl, undecyl, dodecyl and the like.

The term "alkenyl", is used in defining substituents in the present specifications and claims, includes both branched and straight-chain alkenyl groups of from 2 to 12 carbon atoms. Typical alkenyl groups which are encompassed by this term are ethenyl, prop-1-enyl, prop-2-enyl, but-2-enyl, pent-1-nyl, buta-1,3-dienyl, 2-methylpropenyl, allyl, 1-methylethyenyl, crotyl and the like.

The term "alkynyl" is used in defining substituents in the present specification and claims, includes both straight and branch chain alkynyl groups of from 2 to 8 carbon atoms. Typical alkynyl groups which are encompassed by this term are ethynyl, 2-propynyl, hex-2-ynyl, 4-methylpent-1-ynyl, octa-2,4-diynyl and the like.

The term "pseudoaryl" as used in the present specification and claims, includes pyridinyl, pyrrolyl, furanyl, thiophenyl, indolyl, pyrimidinyl, isoindolyl, indolizinyl, imidazolyl, thiazolyl, oxazolyl, isoxazolyl, isothiazolyl, pyronyl, 1,4-dioxanyl, 1,2,4-triazolyl, quinolinyl and isoquinolinyl and the like.

DETAILED DESCRIPTION OF THE INVENTION

This invention relates to substituted 2,4-imidazolidinediones, their preparation and their use as broad spectrum fungicides. In particular, this invention relates to compounds of the formula

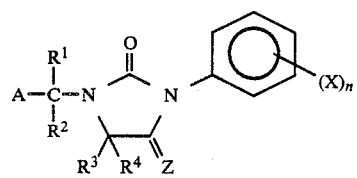

wherein

X is selected from a group comprising halogen, nitro, cyano, $(C_1-C_{12})$alkyl, $(C_1-C_{12})$alkoxy, trihalomethyl, or phenoxy, phenylthio, phenyl, naphthyl, phenyl-$(C_1-C_6)$alkyl optionally substituted on the aromatic moiety with up to three substituents selected from the group comprising halogen, nitro, cyano, $(C_1-C_6)$alkyl, $(C_1-C_6)$alkoxy, and trihalomethyl;

$R^1$ and $R^2$ are independently hydrogen, $(C_1-C_{12})$alkyl, $(C_2-C_{12})$alkenyl, $(C_2-C_8)$alkynyl, cyano, halogen, phenyl, phenyl-$(C_1-C_6)$alkyl, $(C_3-C_{10})$cycloalkyl, and $(C_5-C_{10})$cycloalkenyl;

$R^3$ and $R^4$ are independently hydrogen, alkyl, alkenyl, alkynyl, cyano, halogen, phenyl, phenylalkyl, cycloalkyl, and cycloalkenyl; or $R^3$ and $R^4$ taken together for a $(C_3-C_8)$cycloalkyl ring or a $(C_3-C_8)$cycloalkenyl ring;

A is phenyl or pseudoaryl, or phenyl or pseudoaryl substituted with up to three substitutents selected from the group comprising halogen, nitro, cyano, $(C_1-C_6)$alkyl, $(C_2-C_6)$alkenyl, $(C_2-C_6)$alkynyl, $(C_1-C_6)$alkoxy, and trihalomethyl, or

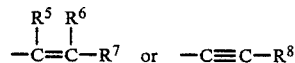

wherein $R^5$, $R^6$, $R^7$, $R^8$ are independently hydrogen, $(C_1-C_6)$alkyl, $(C_2-C_6)$alkenyl, $(C_2-C_6)$alkynyl, cyano, or halogen;

n is either 2 or 3;

Z is O, S, NH, or $CH_2$.

A more preferred embodiment of this invention is the compounds of formula I wherein X is selected from a group consisting of chlorine, bromine, methyl, ethyl, propyl, isopropyl, methoxy, ethoxy, trifluoromethyl, phenoxy, phenylthio, or phenyl;

$R^1$, $R^2$, $R^3$, and $R^4$ are independently hydrogen, methyl, ethyl, n-propyl, isopropyl, prop-1-enyl, or phenyl;

A is phenyl, furanyl, thiophenyl, or

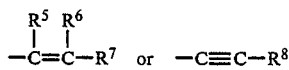

wherein
$R^5$, $R^6$, $R^7$, $R^8$ are independently hydrogen, methyl, ethyl, n-propyl, isopropyl, n-butyl, iso-butyl, sec-butyl, tert-butyl, ethenyl, prop-1-enyl, prop-2-enyl, ethenyl, or propynyl;
n is 2 or 3; and
Z is O or $CH_2$.

A most preferred embodiment of this invention is the compounds of formula I and II wherein X is chlorine; $R^1$, $R^2$, $R^3$, and $R^4$ are independently hydrogen or methyl;
A is ethenyl or ethynyl;
n is 2; and
Z is O or $CH_2$.

Typical compounds encompassed by the present invention include:

3-(3,5-Dichlorophenyl)-1-(2-propynyl)-5-methyl-2,4-imidazolidinedione 1-(3,5-Dichlorophenyl)-4,4-dimethyl-3-propy-2-yl-5-methylene-2-imidazolidinone 3-(3,5-Dichlorophenyl)-1-allyl-5-methyl-2,4-imidazolidinedione 3-(3,5-Dichlorophenyl)-1-(1,1-dimethyl-2-propynyl)-5-methyl-2,4-imidazolidinedione 3-(2,4-Dichlorophenyl)-1-(2-propynyl)-5-allyl-2,4-imidazolidinedione 1-(3,5-Dichlorophenyl)-4,4-dimethyl-3-propy-2-yl-5-thio-2-imidazolidone 1-(3,5-Dichlorophenyl)-3-(2-propynyl)-5-aza-2-imidazolidinone 3-(4-Chlorophenyl)-1-allyl-2,4-imidazolidinedione 3-(3,5-Dimethylphenyl)-1-(2-propynyl)-2,4-imidazolidinedione 3-(3,5-Dichlorophenyl)-1-(2-propynyl)-5,5-pentamethylene-2,4-imidazolidinedione The compounds of the instant invention, when Z is either oxygen or sulphur, can be prepared according to the following reaction scheme (EQ. 1–3):

(Eq. 1)

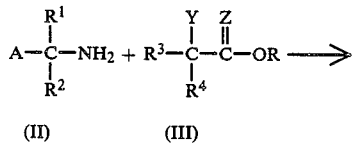

(Eq. 2)

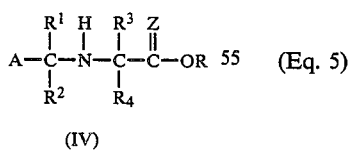

(Eq. 3)

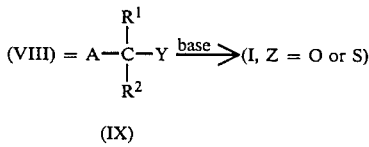

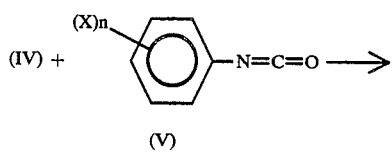

(I, Z = O or S)

In Equation 1 Y is either halogen or another appropriate leaving group and R is hydrogen or alkyl.

Alkylation of a primary amine of structure (II) with an acid, a cycloacid, an ester, or thioester of structure (III) under basic conditions provides amino(thio)acid or amino(thio)ester (IV). Reaction of (IV) with a substituted phenyl isocyanate (V) gives urea (VI) which is readily cyclized to the desired 2,4-imidazolidinedione or its thioketone derivative (I) by heat or by a catalyst.

Alternatively, compounds of the instant invention (I) when Z is oxygen or sulfur, can be synthesized by the following scheme: (Eq. 4–5):

(Eq. 4)

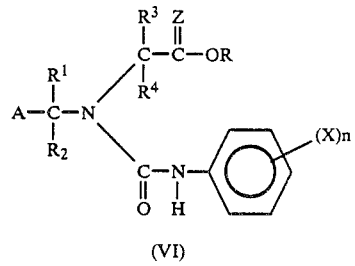

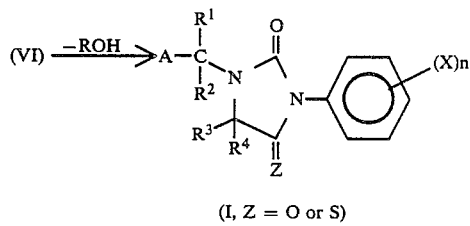

(Eq. 5)

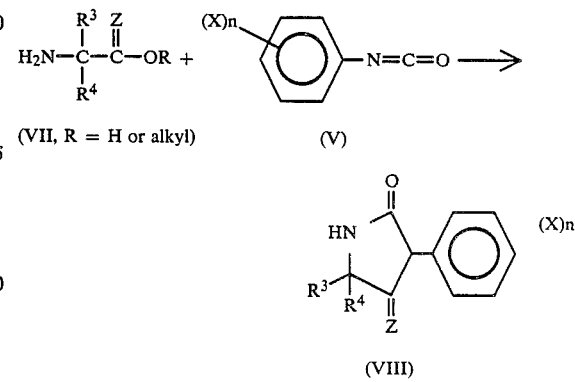

Wherein Y is halogen or appropriate leaving group.

Reaction of an amino acid, an aminothio acid and aminoester or an aminothioester (VII) with a substituted phenylisocyanate (V) gives the parent 2,4-imidazolidinedione or its thioketone derivative (VIII).

Alkylation of (VIII) with a halide or sulfanate under basic conditions produces the desired product (I).

Compounds of the instant invention (I), when Z is either NH or CH₂, can be prepared according to the following scheme; (Eq. 6–7):

(Eq. 6)

$$A-\underset{R^2}{\overset{R^1}{C}}-NH_2 + Y-\underset{R^4}{\overset{R^3}{C}}-C\equiv Q \longrightarrow A-\underset{R^2}{\overset{R^1}{C}}-\overset{H}{N}-\underset{R^4}{\overset{R^3}{C}}-C\equiv Q$$

(II)     (X)     (XI)

(Eq. 7)

(XI) + (V) ⟶

[structure (XII)] ⟶ (I, Z = NH, CH₂)

wherein Q is either N or CH.

Reaction of a primary amine (II) with a nitrile or an acetylene (X) under basic conditions provides aminonitrile or aminoacetylene (XI). When (XI) is allowed to react with a substituted phenyl isocyanate (V), cyano or acetylenic urea (XII) is produced. Compound (XII) can be further cyclized to the desired product (I) by heat or by a catalyst.

Alternatively compounds of the instant invention (I), when Z is either NH or CH₂ can be prepared according to the following scheme (Eq. 8–9):

(Eq. 8)

$$H_2N-\underset{R^4}{\overset{R^3}{C}}-C\equiv Q + (V) \longrightarrow$$

(XIII)

[structure (XIV)]

↓

[structure (XV)]

(Eq. 9)

$$(XV) + A-\underset{R^2}{\overset{R^1}{C}}-Y \xrightarrow{base} (I, Z = NH \text{ or } CH_2)$$

(IX)

wherein Q is N or CH and Y is halogen or another leaving group.

An aminonitrile or an aminoacetylene (XIII) is first reacted with a substituted phenylisocyanate (V) to give a cyano urea or a propargyl urea (XIV) which can be cyclized to give the corresponding imino or methylene imidazolidinone (XV) (Equation 8). Alkylation of (XV) with a halide or sulfonate (IX) under basic conditions produces the desired product (I) (Eq. 9).

The following examples are provided to illustrate the methods of preparation of the compounds of this invention. These examples are not intended to limit the breadth or scope of the instant invention. The temperatures expressed in these examples are in degrees centigrade.

EXAMPLE 1

Preparation of 3-(3,5-Dichlorophenyl)-1-(2-propynyl)-5-methyl-2,4-imidazolidinedione $$HC\equiv CCH_2NH_2 + Br-\underset{}{\overset{CH_3}{CH}}COOCH_3 \longrightarrow HC\equiv CCH_2\overset{H}{N}-\overset{CH_3}{CH}COOCH_3$$

↓ [3,5-dichlorophenyl isocyanate]

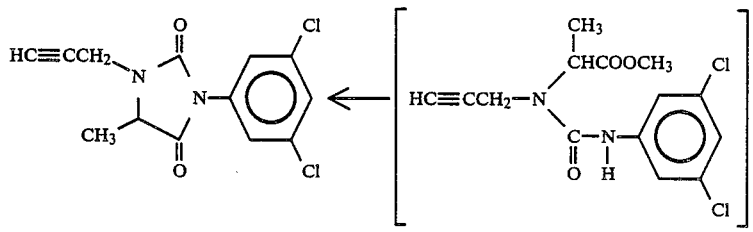

A. Methyl 2-propargylaminopropionate

Into a 250 ml round bottom flask are placed 26 g (0.47 mole) of propargylamine, 78.8 g (0.47 mole) of methyl 2-bromopropionate, and 39.7 g (0.47 mole) of sodium bicarbonate. The reaction mixture is heated at 80° C. overnight. It is cooled and poured into 200 ml of water. Extraction with ether provides 45 g of crude product which is further purified by vacuum distillation (94°–95°/3 mm) to give 25 g of desired product.

B. 3-(3,5-Dichlorophenyl)-1-(2-propynyl)-5-methyl-2,4-imidazolidinedione

To a solution of 10 g (0.07 mole) of methyl 2-propargylaminopropionate in 100 ml of toluene with 2 drops of stannous octoate is added 14.5 g (0.077 mole) of 3,5-dichlorophenylisocyanate in small portions. The resulting mixture is heated at 100° for 3 hours. It is then washed with water twice and dried over sodium sulfate. Solvent is evaporated to give a thick yellow oil. Material is further purified by passing it through a silica gel column using 30/70 ethyl acetate/hexane as solvent to give 18 g of a light yellow oil which solidifies on standing. The solids are triturated in boiling hexane and collected by filtration, mp 105°–6°. NMR and elemental analysis confirm the desired structure.

nmr (DMSO) (δ) 1.6 (d, 3H), 3.3 (m, 1H), 4.3 (m, 3H), 7.6 (m, 3H).

EXAMPLE 2

Preparation of 1-(33,5-Dichlorophenyl)-4,4-dimethyl-3-propyn-2-yl-5-methylene 2-imidazolidione

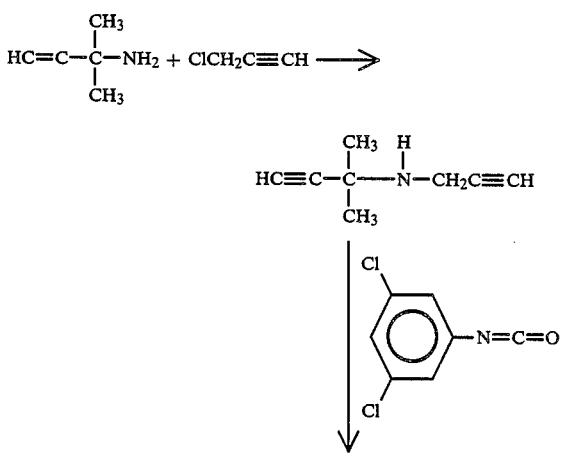

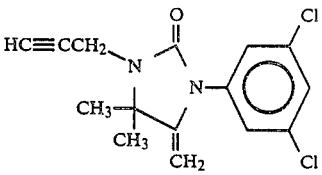

A. α,α-Dimethylpropargyl propargyl amine

A solution of 93 g (1.25 mole) of propargyl chloride is added to a mixture of 100 g (1.2 mole) of α,α-dimethylpropargyl amine, 126 g (1.5 mole) of sodium bicarbonate and 200 ml of ethanol. The reaction mixture is heated to reflux for 4 hours. Solids are filtered and the filtrate is concentrated under vacuum. The concentrated oil is further purified by distilling at reduced pressure (20 mm) twice to give 18 g of pure product.

B. 1-(3,5-Dichlorophenyl)-4,4-dimethyl-3-propyn-2-yl-5-methylene-2-imidazolidinone To a solution of 8 g (0.066 mole) of α,α-dimethylpropargyl propargyl amine in 100 ml of toluene with 2 drops of stannous octoate and 2 ml of triethylamine is added 14 g (0.075 mole) of 3,5-dichlorophenyl isocyanate in small portions. The resulting reaction mixture is heated to reflux overnight. The solids formed are filtered and the filtrate is concentrated under vacuum to give a thick brown oil. When the material is triturated with 20/80 ethyl acetate/hexane, yellow precipitates separate. Material is collected by filtration and dried to give 5.5 g of the expected product, m.p. 78°–80°.

nmr (CDCl₃) (δ) 1.5 (S, 6H), 2.2 (t, 1H), 4.1 (m, 4H), 7.3 (S, 3H).

EXAMPLE 3

Preparation of 3-(3,5-Dichlorophenyl)-1-allyl-5-methyl-2,4-imidazolidinedione

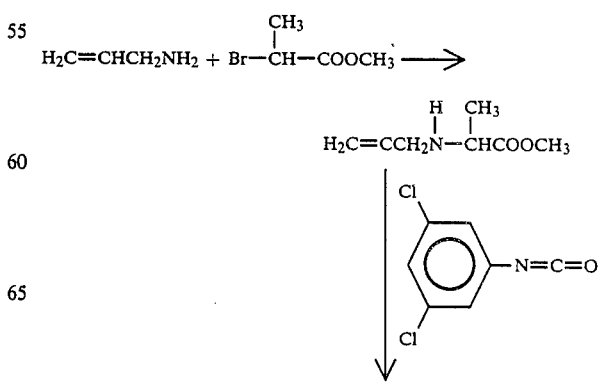

-continued

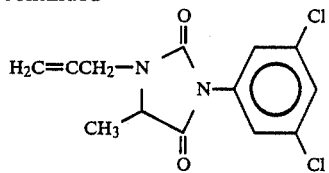

A. Methyl 2-allylaminopropionate

To a mixture of 10 g (0.18 mole) of allylamine, 10.8 g (0.2 mole) of sodium bicarbonate in 50 ml of ethanol is added 30 g (0.18 mole) of methyl 2-bromopropionate dropwise. The resulting mixture is heated under reflux for 5 hours. The reaction mixture is cooled, poured into water, and extracted with ether. The combined ether extracts are washed with water and dried over magnesium sulfate. The drying agent is filtered and the filtrate is concentrated under reduced pressure to give 15.5 g of a light yellow oil. This material is further purified by distillation to give 10.5 g of pure product.

B. 3-(3,5-Dichlorophenyl)-1-allyl-5-methyl-2,4-imidazolidinedione

To a solution of 10.5 g (0.073 mole) of methyl 2-allylaminopropionate in 50 ml of toluene is added 15 g (0.08 mole) of 3,5-dichlorophenylisocyanate in small portions. The resulting mixture is heated to reflux for 2 hours. The reaction mixture is cooled and filtered. The filtrate is concentrated under vacuum to give 25 g of a yellow oil. This material is further purified by passing it through a silica gel column using 40/60 ethyl acetate/hexane as the solvent followed by trituration with hexane/ether to give 18 g of a light yellow solid., m.p. 78°–80°.

nmr (CDCl$_3$) ($\delta$) 1.5 (d, 3H), 4.0 (m, 3H), 5.5 (m, 3H), 7.4 (m, 3H).

cinia graminis f. sp. tritici race 15 B-2) on wheat seedlings.

In evaluating fungicidal efficacy of the compounds of the instant invention, the compounds were dissolved in a solvent composed of a one-to-one mixture of acetone and methanol and diluted with an equal quantity of water to give a 300 ppm. concentration. The solutions were used to spray the plants to run off at a volume of about a 150 gallons per acre. The general procedure is to take potted plants in the proper condition of growth for susceptibility to the fungal disease to be evaluated, and to spray these plants on a moving belt and to allow them to dry. The plants are then inoculated with the fungal spores and then allowed to incubate until the disease has developed and the extent of disease control can be evaluated.

The following test methods were employed in evaluating the fungicidal activity of the compounds of this invention:

EXAMPLE A

Barley Net Blotch (Helminthosporium teres) (BH)

Barley plants (var. Besbar) are trimmed to a height approximately 2½ inches, 24 hours prior to chemical application. This procedure provides plants of a uniform height and permits rapid inoculation of treated plants.

Helminthosporium teres is cultured on potato-dextrose agar (PDA) slants for 14 days at ambient temperature and low light intensity. Spores are harvested by adding deionized water to the PDA slants and scraping the agar surface with a rubber policeman or similar blunt object. The spore suspension is filtered through cheesecloth to remove mycelial and agar fragments and then adjusted to a concentration of 15–20,000 spores/ml. One drop (0.05 ml) of Tween 80 is added to 100 cc inoculum to provide a more even spore distribution on the surface of the barley leaves.

TABLE 1

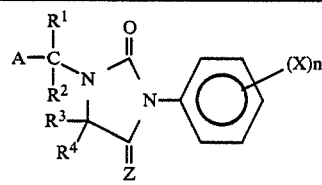

| | | | | | | | | | | Elemental Analysis, Calc'd (Found) | | | | |
|---|---|---|---|---|---|---|---|---|---|---|---|---|---|---|
| Example | Formula | Z | (X)n | A | R$^1$ | R$^2$ | R$^3$ | R$^4$ | mp (°C.) | C | H | Cl | N | O |
| 1 | C$_{13}$H$_{10}$Cl$_2$N$_2$O$_2$ | O | 3,5-Cl$_2$ | C≡CH | H | H | CH$_3$ | H | 105–6 | 52.54 | 3.39 | 23.86 | 9.43 | 10.77 |
| | | | | | | | | | | (52.46) | (3.35) | (23.59) | (9.37) | (10.62) |
| 2 | C$_{15}$H$_{14}$Cl$_2$N$_2$O | CH$_2$ | " | C=CH | H | H | CH$_3$ | CH$_3$ | 78–80 | 52.27 | 4.56 | 22.93 | 9.06 | 5.17 |
| | | | | | | | | | | (57.97) | (4.45) | (23.47) | (9.24) | (5.88) |
| 3 | C$_{13}$H$_{12}$N$_2$O$_2$ | O | " | CH=CH$_2$ | H | H | CH$_3$ | H | 78–80 | 52.19 | 4.04 | 23.70 | 9.37 | 10.70 |
| | | | | | | | | | | (51.81) | (3.94) | (23.89) | (9.11) | (11.33) |
| 4 | C$_{15}$H$_{19}$Cl$_2$N$_2$O$_2$ | O | " | C≡CH | CH$_3$ | CH$_3$ | CH$_3$ | H | 114.6 | 55.57 | 4.04 | 21.87 | 8.64 | 9.87 |
| | | | | | | | | | | (55.54) | (4.20) | (21.81) | (9.00) | (10.23) |

The 2,4-imidazolidinediones of the instant invention are broad spectrum fungicides which possess a high degree of activity against phytopathogenic fungi. These compounds are particularly effective at rates of application from about 50 to about 300 ppm. in controlling barley net blotch (Helminthosporium teres) on barley plants, bean powdery mildew (Erysiphe polygoni) on bean plants, grape downy mildew (Plasmopora viticola) on grape seedlings, tomato late blight (Phytophthora infestans) on tomato seedlings and wheat stem rust (Puc- The barley plants are inoculated by spraying the foliage of the plants with a hand sprayer until small droplets of inoculum are observed on the leaves. Inoculated plants are incubated in a humid environment at 75°–80° F. for 24 hours prior to being placed in the greenhouse at 70°–75° F.

Treatment comparisons are made 6–7 days afer inoculation. Typical barley net blotch symptoms initially appear as irregular sunken water-soaked areas which become necrotic as the lesions enlarge.

Examples 1 and 3 of the present invention have shown greater than 95% control of barley net blotch at a 300 ppm rate of application.

EXAMPLE B

Bean Powdery Mildew (*Erysiphe polygoni*) (BPM)

Bean plants (var. Dwarf Hort) are thinned to two plants per pot 24 hours prior to chemical application.

*Erysiphe polygoni* is cultured on bean leaves for 10–21 days under existing greenhouse conditions. Spores are harvested by adding deionized water containing 0.5 ml of Tween 80 per 500 ml water to a quart jar containing excised mildew infested bean leaves. The resulting suspension is filtered through cheesecloth to remove plant debris and adjusted to $2-2.5 \times 10^4$ spores per ml.

Bean plants are inoculated by spraying the leaves and stems with inoculum until a uniform film of inoculum is observed on the plant. Inoculated plants are maintained under existing greenhouse conditions.

Treatment comparisons are made 8–10 days after inoculation. Typical bean powdery mildew signs are circular white mycelial mats (fructifications) on the leaf surface.

Examples 1 and 4 of the present invention have shown greater than 95% control of bean powdery mildew at a rate of application of 300 ppm.

EXAMPLE C

Grape Downy Mildew (*Plasmopora viticola*) (GDM)

Grape seedlings 4–5 inches tall are used.

*Plasmopora viticola* is cultured on grape leaves for 7 days at 65°–75° F. in a growth room at moderate light intensity. Spores are harvested by adding deionized water and scraping the leaf surface with a camel's hair brush. The spore suspension is filtered through cheesecloth to remove plant debris and adjusted to a concentration of 100–125,000 spores per ml.

The grape plants are inoculated by spraying the leaves with a hand held air brush until small uniform droplets of inoculum are observed on the leaves. The inoculated plants are incubated in a humid environment at 65°–75° F. for 48 hours prior to being placed in a growth room.

Treatment comparisons are made 7 days after inoculation. Typical grape downy mildew symptoms appear on the upper leaf surface as pale-yellow spots variable in size and form, frequently circular without a distinct line of demarcation. Under humid conditions the lower leaf surface is covered by conspicuous fungal growth.

Example 3 of the present invention has shown greater than 95% control of grape downy mildew at an application rate of 300 ppm.

EXAMPLE D

Tomato Late Blight (*Phytophthora infestans*) (TLB)

Tomato (var. Rutgers) seedlings, 2½–3 inches tall, are fertilized with a water soluble fertilizer 4–5 days prior to chemical application to promote rapid succulent growth and better symptom expression.

The pathogen is grown on lima bean agar for 12–15 days at 60° F. and the fungal growth is removed by the agitation of a rubber policeman on a glass rod over the surface of the agar in the presence of deionized water. The inoculum is strained through cheesecloth to remove mycelial and agar fragments and the spore concentration adjusted to 50–60,000 spores/ml.

The spore suspension is applied to a DeVilbiss atomizer at 8–10 psi air pressure onto the leaf undersurface until fine droplets are formed.

Inoculated seedlings are placed in a humid environment at 60°–62° F. for 40–45 hours, prior to being placed in the greenhouse at 70°–75° C.

Treatment comparisons are made 5–6 days afer inoculation. Initially, typical tomato late blight symptoms appear as irregular, greenish-black, water-soaked patches which enlarge and become brown, with a firm corrugated surface. Severe infection will resemble frost damage.

Example 2 of the present invention has shown at least 90% control of tomato late blight at an application rate of 300 ppm.

EXAMPLE E

Wheat Stem Rust (*Puccinia graminis* f. sp. *tritici* race 15B-2) (WSR)

Seven-day-old wheat plants (var. Wanser) are trimmed to approximately 2½ inches, 24 hours prior to chemical application to provide a uniform plant height and to faciliate uniform inoculation.

Wheat stem rust is cultured on wheat seedlings (var. Wanser) for a period of 14 days under existing greenhouse conditions.

A spore suspension of *Puccinia graminis* f. sp. *tritici* race 15B-2 is made by excising infected wheat leaves and placing the leaves into a pint jar containing water and the surfactant "Tween 80" (1 drop/100 cc). The surfactant serves to free the rust urediospores from the sori and improves inoculum retention when applied to plant foliage. The resulting spore suspension is filtered through cheesecloth to remove the leaves and assorted other plant debris. The spore concentration is not adjusted, but a minimum of $2.5 \times 10^4$ spores per ml are required to obtain an acceptable disease level.

Wheat plants are inoculated by applying the stem rust spore suspension until run-off, with a DeVilbiss atomizer at 5 psi air pressure. After inoculation, the plants are placed into a humid environment at approximately 68° F. A timer is used to permit 12 hours of continuous darkness followed by a minimum of 3–4 hours of light with an intensity of 500 ft. candles. The temperature in the chamber should not exceed 85° F. At the end of the light period, the fogger is turned off and vented to allow the plants to dry slowly prior to being placed into a greenhouse environment.

The plants are permitted to grow under greenhouse condition for a period of 2 weeks prior to making treatment comparisons. Wheat stem rust is characterized by brick red spores in an irregularly shaped sori on the leaves and stems of the wheat seedlings.

Examples 1 and 3 of the present invention have shown greater than 95% control of wheat stem rust at an application rate of 300 ppm.

The compounds of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers Annual."

In general, the compounds of this invention can be dissolved in certain solvents such as acetone, methanol, ethanol, dimethylformamide, pyridine or dimethyl sulfoxide and such solutions extended with water. The concentrations of the solution can vary from 1% to 90% with a preferred range being 5 to 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of 3-(3,5-dichlorophenyl)-1-(2-propynyl)-5-methyl-2,4-imidazolidinedione, 45 parts of a synthetic precipitated hydrated silicon dioxide sold under the trademark Hi-Sil ®, and 5 parts of sodium lignosulfonate (Marasperse ® N-22). In another preparation of a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the 2,4-imidazolidinediones and salts and complexes thereof with finely divided inert solids which can be organic or inorganic in nature. Materials useful for this purpose include botanical flours, silicas, silicates, carbonates and clays. One convenient method of preparing a dust is to dilute a wettable power with a finely divided carrier. Dust concentrates containing 20% to 80% of the active ingredient are commonly made and are subsequently diluted to 1% to 10% use concentration.

The 2,4-imidazolidinediones can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method of application and diseases to be controlled, but the preferred effective amount is usually about 0.1 lb. to 50 lbs. per acre of the active ingredient.

As a seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre.

As a foliar fungicide, the toxicant is usually applied to growing plants at a rate of 0.25 to 10 lbs. per acre.

Fungicides which can be combined with the fungicides of this invention includes:

(a) dithiocarbamates and derivatives such as: ferric dimethyldithiocarbamate (ferbam), zinc, dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalamide (captan), N-Trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, -(phenyl)- -(2,4-dichlorophenyl)-5-pyrimidinyl-methanol (triarimol), cis-N-[(1,1,2,2-tetrachloroethyl)thio]-4-cyclohexene-1,2-dicarboximide, 3-[2-(3,5-dimethyl-2-oxycyclohexyl-2-hydroxy)glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclodecyl-2,6-dimethylmorpholine (dodemorph), and 6-methyl-2-oxo-1,3-dithiolo[4,5-b]-quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds calcium cyanamide, lime sulfur, 1,2-bis(3-methoxycarbonyl-2-thioureido) benzene (thiophanate-methyl).

The compounds of this invention can be advantageously employed in various ways. Since these compounds possess broad spectrum fungicidal activity, they can be employed in the storage of cereal grain. These complexes can also be employed as fungicides in turf, fruit orchard, vegetables and golf course applications. Other applications of the compounds of this invention will suggest themselves to those skilled in the art of agriculture and horticulture.

I claim:

1. A compound of the formula

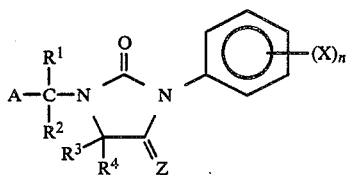

wherein:

X is selected form the group consisting of halogen, nitro, cyano, $(C_1-C_{12})$alkyl, $(C_1-C_{12})$alkoxy, trihalomethyl, and phenoxy, phenylthio, phenyl, naphthyl, and phenyl-$(C_1-C_6)$alkyl optionally substituted with up to three substituents selected from the group consisting of halogen, nitro, cyano, $(C_1-C_6)$alkyl, $(C_1-C_6)$alkoxy and trihalomethyl;

$R^1$ and $R^2$ are independently hydrogen, $(C_1-C_{12})$alkyl, $(C_2-C_{12})$alkenyl, $(C_2-C_8)$alkynyl, cyano, halogen, phenyl, phenyl$(C_1-C_6)$alkyl, $(C_3-C_{10})$cycloalkyl or $(C_5-C_{10})$cycloalkenyl;

$R^3$ and $R^4$ are independently hydrogen, $(C_1-C_{12})$alkyl, $(C_2-C_{12})$alkenyl, $(C_2-C_8)$alkynyl, cyano, halogen, phenyl, phenyl$(C_1-C_6)$alkyl, $(C_3-C_{10})$cycloalkyl or $(C_5-C_{10})$cycloalkenyl, or $R^3$ and $R^4$ taken together form a $(C_3-C_8)$cycloalkyl or $(C_3-C_8)$cycloalkenyl ring;

A is selected from the group consisting of pyridinyl, pyrrolyl, furanyl, thiophenyl, indolyl, pyrimidinyl, isoindolyl, indolizinyl, imidazolyl, triazolyl, oxazolyl, isoxazolyl, isothiazolyl, 1,4-dioxamyl, 1,2,4-triazole, quinolinyl and isoquinolinyl optionally substituted with up to three substituents selected from the group consisting of halogen, nitro, cyano, $(C_1-C_6)$alkyl, $(C_2-C_6)$alkenyl, $(C_2-C_6)$alkynyl, $(C_1-C_6)$alkoxy and trihalomethyl, or

wherein $R^8$ is hydrogen, $(C_1-C_{12})$alkyl, $(C_2-C_{12})$alkenyl, $(C_2-C_{10})$alkenyl, cyano or halogen;

n is an integer of 0 to 3;

Z is O, S, NH, or $CH_2$.

2. The compound of claim 1 wherein
A is $-C{\equiv}C-R^8$; and
Z is O or S.

3. A compound of the formula

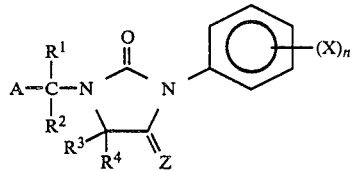

wherein:

X is selected form a group consisting of chlorine, bromine, methyl, ethyl, n-propyl, isopropyl, methoxy, ethoxy, trifluoromethyl and phenoxy;

$R^1$, $R^2$, $R^3$ and $R^4$ are independently hydrogen, methyl, ethyl, n-propyl, isopropyl, ethynyl, prop-1-enyl or phenyl;

A is furanyl, thiophenyl or

wherein $R^8$ is hydrogen, $(C_1-C_6)$alkyl, $(C_2-C_6)$alkynyl, $(C_2-C_6)$alkenyl, cyano, chlorine or bromine;

n is 2 or 3; and

Z is O or $CH_2$.

4. A compound according to claim 3 wherein
X is chlorine;
$R^1$, $R^2$, $R^3$ and $R^4$ are independently hydrogen or methyl;
A is ethynyl of the formula:

wherein $R^8$ is hydrogen, methyl, ethyl, n-propyl, isopropyl, n-butyl, iso-butyl, secbutyl, tert-butyl, ethenyl, prop-1-enyl, prop-2-enyl, ethenyl, or propynyl;

n is 2; and

Z is O or $CH_2$.

5. A compound according to claim 4 wherein $R^1$, $R^2$ and $R^4$ are hydrogen, $R^3$ is methyl, A is ethynyl and Z is oxygen.

6. A compound according to claim 4 wherein $R^1$, $R^2$ and $R^3$ are methyl, $R^4$ is hydrogen, A is ethynyl and Z is oxygen.

7. A compound according to claim 4 wherein $R^1$ and $R^2$ are hydrogen, $R^3$ and $R^4$ are methyl, A is ethynyl and Z is $CH_2$.

8. The compound of claim 3 wherein
A is $-C{\equiv}C-R^8$.

9. A compound of the formula:

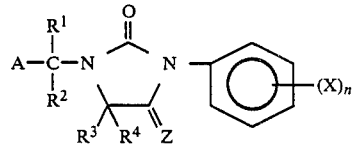

wherein

X is selected from the group consisting of chlorine, bromine, nitro, cyano, methyl, ethyl, n-propyl, isopropyl, methoxy, ethoxy, trifluoromethyl and phenoxy;

$R^1$ and $R^2$ are independently hydrogen, $(C_1-C_8)$alkyl, $(C_2-C_8)$alkenyl, $(C_2-C_6)$alkynyl, cyano, chlorine, bromine, phenyl, phenyl$(C_1-C_6)$alkyl, $(C_3-C_8)$cycloalkyl or $(C_5-C_8)$cycloalkenyl;

$R^3$ and $R^4$ are independently hydrogen, $(C_1-C_8)$alkyl, $(C_2-C_8)$alkenyl, $(C_2-C_6)$alkynyl, cyano, chlorine, bromine, phenyl, phenyl$(C_1-C_6)$alkyl, $(C_3-C_8)$cycloalkyl or $(C_5-C_8)$cycloalkenyl, or $R^3$ and $R^4$ taken together form a $(C_3-C_8)$cycloalkyl or $(C_3-C_8)$cycloalkenyl ring;

A is selected from the group consisting of furanyl, thiophenyl or —C≡C—$R^8$ wherein $R^8$ is hydrogen, $(C_1-C_6)$alkyl, $(C_2-C_6)$alkenyl, $(C_2-C_6)$alkynyl, cyano, chlorine or bromine;

n is 2 or 3; and

Z is O, S, NH or $CH_2$.

10. A fungicidal composition for controlling phytopathogenic fungi which comprises an agronomically acceptable carrier and, as an active ingredient, a fungicidally effective amount of a compound according to claim 1.

11. A fungicidal composition for controlling phytopathogenic fungi which comprises an agronomically acceptable carrier and, as an active ingredient, a fungicidally effective amount of a compound according to claim 4.

12. A fungicidal composition for controlling phytopathogenic fungi which comprises an agronomically acceptable carrier and, as an active ingredient, a fungicidally effective amount of a compound according to claim 9.

13. A fungicidal composition for controlling phytopathogenic fungi which comprises an agronomically acceptable carrier and, as an active ingredient, a fungicidally effective amount of a compound according to claim 3.

* * * * *